US009669167B2

(12) United States Patent
Lockhart et al.

(10) Patent No.: US 9,669,167 B2
(45) Date of Patent: Jun. 6, 2017

(54) MULTIFUNCTIONAL GLUCOSE MONITORING SYSTEM AND METHOD OF USING THE SAME

(71) Applicant: Becton, Dickinson and Company, Franklin Lakes, NJ (US)

(72) Inventors: Artis Lockhart, Durham, NC (US); Lawrence Monahan, Fuquay Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 43 days.

(21) Appl. No.: 14/649,883

(22) PCT Filed: Dec. 6, 2012

(86) PCT No.: PCT/US2012/068221
§ 371 (c)(1),
(2) Date: Jun. 4, 2015

(87) PCT Pub. No.: WO2014/088581
PCT Pub. Date: Jun. 12, 2014

(65) Prior Publication Data
US 2015/0347714 A1    Dec. 3, 2015

(51) Int. Cl.
*G06F 19/00* (2011.01)
*C12Q 1/54* (2006.01)
(Continued)

(52) U.S. Cl.
CPC ..... *A61M 5/31533* (2013.01); *A61B 5/14532* (2013.01); *A61B 5/4839* (2013.01);
(Continued)

(58) Field of Classification Search
CPC .......... A61M 5/31533; A61M 5/31525; A61B 5/14532; A61B 5/4839; C12Q 1/54; G01D 7/00; G06F 19/3468
(Continued)

(56) References Cited

U.S. PATENT DOCUMENTS 6,113,578 A * 9/2000 Brown ............... A61B 5/14532
222/23
2007/0088285 A1    4/2007 Sharp et al.
(Continued)

FOREIGN PATENT DOCUMENTS

WO    WO-2011058560 A1    5/2011

*Primary Examiner* — Jill Warden
*Assistant Examiner* — Jacqueline Brazin
(74) *Attorney, Agent, or Firm* — Dickinson Wright PLLC

(57) ABSTRACT

A multifunctional glucose monitoring system and method of measuring glucose level, determining insulin dosage, and indicating insulin dosage on a syringe is disclosed. The multifunctional glucose monitoring system includes standard functionality with respect to acquiring a blood glucose reading. However, in addition, the multifunctional glucose monitoring system includes a dosage algorithm for calculating an insulin dosage based on the blood glucose reading and any other useful parameters, and includes a built-in marking device for marking the calculated dosage level on the barrel of an insulin syringe that is installed in the body of the multifunctional glucose monitoring system. A method includes the steps of measuring the glucose level, determining an insulin dosage, and indicating the insulin dosage on a syringe.

17 Claims, 7 Drawing Sheets

(51) Int. Cl.
  *G01D 7/00* (2006.01)
  *A61M 5/315* (2006.01)
  *A61B 5/145* (2006.01)
  *A61B 5/00* (2006.01)
  *A61M 5/178* (2006.01)

(52) U.S. Cl.
  CPC ........... *A61M 5/31525* (2013.01); *C12Q 1/54* (2013.01); *G01D 7/00* (2013.01); *G06F 19/3468* (2013.01); *A61M 5/1782* (2013.01); *A61M 5/31511* (2013.01); *A61M 5/31535* (2013.01); *A61M 5/31555* (2013.01); *A61M 5/31556* (2013.01); *A61M 2205/14* (2013.01); *A61M 2205/3553* (2013.01); *A61M 2205/3561* (2013.01); *A61M 2205/52* (2013.01); *A61M 2205/584* (2013.01)

(58) Field of Classification Search
  USPC ......................................................... 422/405
  See application file for complete search history.

(56) References Cited

U.S. PATENT DOCUMENTS

| | | | | |
|---|---|---|---|---|
| 2009/0303299 A1* | 12/2009 | Gilson | ................. | B41J 2/17513 347/86 |
| 2009/0312713 A1* | 12/2009 | Greutert | ................. | A61J 3/007 604/189 |
| 2011/0184343 A1* | 7/2011 | Veit | ........................ | A61B 5/157 604/66 |
| 2012/0279103 A1 | 11/2012 | Seidl | | |

\* cited by examiner

MULTIFUNCTIONAL GLUCOSE MONITORING SYSTEM AND METHOD OF USING THE SAME

FIELD OF THE INVENTION

The present invention relates generally to a blood glucose monitoring system, and more particularly to a multifunctional glucose monitoring system and method for measuring glucose level, determining insulin dosage, and indicating insulin dosage on a syringe.

BACKGROUND OF THE INVENTION

The incidence of diabetes mellitus is increasing rapidly in developed countries due to increasing obesity, inactive lifestyles, and an aging population. Estimates by the World Health Organization have shown the current global prevalence of diabetes is 3% (194 million people) and is expected to increase in prevalence to 6.3% by 2025. As the incidence of diabetes increases, a corresponding increase in diabetes monitoring and care will be needed.

The goal of any type of diabetes care is to keep blood glucose levels as normal as possible. Complications of diabetes may be more prevalent if blood glucose is not controlled. Some examples of complications are high blood pressure, stroke, eye disease/blindness, kidney disease, heart disease, food disease and amputations, complications of pregnancy, skin and dental disease.

Those who suffer from diabetes must control blood glucose levels on a daily, and sometimes hourly, basis. Insulin is only effective if injected directly into the bloodstream where it may be used by the body to neutralize the effects of excessive blood sugar accumulation. Those who suffer from diabetes and their caregivers must become adept at determining the diabetic's blood glucose level, calculating the correct dosage of insulin required to help return the level to a normal range, loading a syringe with the calculated dosage, and administering the calculated dose through the use of the loaded syringe.

To determine the amount of insulin that is required, a user or caregiver must typically use a glucose monitoring system (aka glucose meter). To test glucose levels with a typical meter, blood is placed on a disposable test strip and placed in the meter. The test strips are coated with suitable chemicals, such as glucose oxidase, dehydrogenase, or hexokinase that combine with glucose in the blood. The meter measures how much glucose is present based on the reactions with these chemicals. Upon receiving the glucose reading, the user or caregiver may determine the amount of insulin required by the user by calculating the dosage required to modify the glucose level to a level in the normal range. The user or caregiver may then load that dose of insulin into a syringe and inject the user.

A concern in the use of a simple glucose meter is that there is no current device that is capable of giving a glucose reading and calculating the insulin dosage from that reading in a single device. An additional concern is that a user or caregiver may have difficulty seeing the markings on a syringe barrel and, subsequently, have difficulty determining when the appropriate dose has been drawn into the syringe barrel. A final concern is that the user, whether it is the diabetic or a caregiver, may be distracted and draw an inaccurate amount of the compound into the syringe barrel through simple inattention to the markings on the barrel. Therefore, new approaches are needed to improve the functionality and convenience of glucose meters.

BRIEF DESCRIPTION OF THE INVENTION

In one embodiment a multifunction glucose meter is provided. The multifunction glucose meter may include a syringe port formed in a body of the multifunction glucose meter, wherein the syringe port is configured to accept a syringe; and a marking device, wherein the marking device is configured to place a mark on an exterior surface of a barrel of the syringe inserted into the syringe port. The device may further include a drive mechanism operatively connected to the marking device and configured to move the marking device along the length of the barrel of the syringe and into contact with the exterior surface of the barrel of the syringe inserted into the syringe port. The device may further include a test port; transducer; display and controller, wherein the test port is in operative communication with the transducer, and wherein the transducer and display are operatively connected to the controller. The device may further include a dosage algorithm that is interfaced with or integrated into the controller, wherein the dosage algorithm calculates an insulin dosage. The dosage algorithm may be implemented in at least one of software and/or hardware. The marking device may be linearly positioned in accordance with the calculated insulin dosage, and the marking device may be positioned so as to place the marking device in contact with the exterior surface of the barrel of the syringe. The mark may be calibrated to indicate a particular dosage of insulin. The calibration of the insulin dosage may be based on a glucose reading performed by the glucose meter. The mark on the barrel of the syringe preferably indicates a point at which the barrel of the syringe is to be filled to provide the insulin dosage in accordance with the glucose reading from the glucose meter. The device may further include a communication interface connected to the controller. The device may further include at least one of a syringe sensor, ink level sensor, and marking strip level sensor. The device may further include one or more indicators corresponding to the at least one of the syringe sensor, ink level sensor, and marking strip level sensor, wherein the one or more indicators are one of visual, audible, tactile, or combination thereof. The marking device may be disposed internally to the glucose meter and may be proximate to the syringe port. The syringe accepted into the syringe port may be rotatable. The device may further include a syringe drive mechanism proximate the syringe port and configured for rotating the syringe. The marking device may be rotatable about the exterior surface of the barrel of the syringe. The marking device preferably causes a mark on at least a portion of the barrel of the syringe. The mark may include an ink marking, wherein the ink marking may be a high visibility/contrast color. The mark may include a strip adhered to the exterior surface of the barrel of the syringe. The strip may include a substantially transparent window formed therein.

In another embodiment a multifunction glucose meter system is provided. The multifunction glucose meter system may include a glucose meter having a syringe port; a syringe removeably emplaced within the syringe port; and a marking device wherein the marking device is configured to place a mark on an exterior surface of the barrel of the syringe inserted into the syringe port.

In yet another embodiment a method of determining a medication dose and marking an indication of said dose on a syringe is provided. The method may include the steps of inserting a blood sample from a user into a glucose meter and obtaining a glucose reading from the blood sample; calculating an insulin dosage in accordance with the glucose reading; inserting a syringe into a syringe port within the glucose meter; positioning a marking device internal to the glucose meter in accordance with the calculated insulin dosage and wherein the marking device is disposed such that the marking device is in contact with the exterior surface of the barrel of the syringe; marking at least a portion of the exterior surface of the barrel of the syringe with a mark at a point that indicates a dosage of insulin calibrated in accordance with the glucose reading; and removing the marked syringe from the syringe port and filling the barrel of the syringe to the mark on the barrel of the syringe in preparation for injecting the dose. The marking device may be a marking pen. The marking device may be a marking strip wherein the marking strip may be colored or may have a transparent window in the strip to view the tip of a plunger within the barrel of the syringe. The marking device may include an indicator to inform the user when the ink or strip level of the marking device is low. The syringe accepted into the syringe port may be rotatable through an arc of up to about 360 degrees. The rotation of the syringe preferably causes the marking device to place a mark on at least a portion of the circumference of the exterior surface of the barrel of the syringe. The syringe may be rotatable by one of manual interaction or automatically. The glucose meter may further include a sensor to sense the full insertion of the syringe into the syringe port and the sensor may include an indicator, wherein the indicator may be one of visual, audible, tactile, or combination thereof. The marking device may be prevented from marking the barrel of the syringe if the sensor does not sense the full insertion of the syringe into the syringe port.

BRIEF DESCRIPTION OF THE DRAWINGS

Various inventive embodiments disclosed herein, both as to its organization and manner of operation, together with further objectives and advantages, may be best understood by reference to the following description, taken in connection with the accompanying drawings as set forth below.

DETAILED DESCRIPTION OF THE INVENTION

A multifunctional glucose monitoring system and method of measuring glucose level, determining insulin dosage, and indicating insulin dosage on a syringe is disclosed. The multifunctional glucose monitoring system includes standard functionality with respect to acquiring a blood glucose reading. However, in addition, the multifunctional glucose monitoring system includes a dosage algorithm for calculating an insulin dosage based on the blood glucose reading and any other useful parameters, and includes a built-in marking device for marking the calculated dosage level on the barrel of an insulin syringe. The multifunctional glucose monitoring system is user friendly; in particular the multifunctional glucose monitoring system may include automation features wherein the ease of use is maximized for all users regardless of the user's range of motion.

Figure 1:
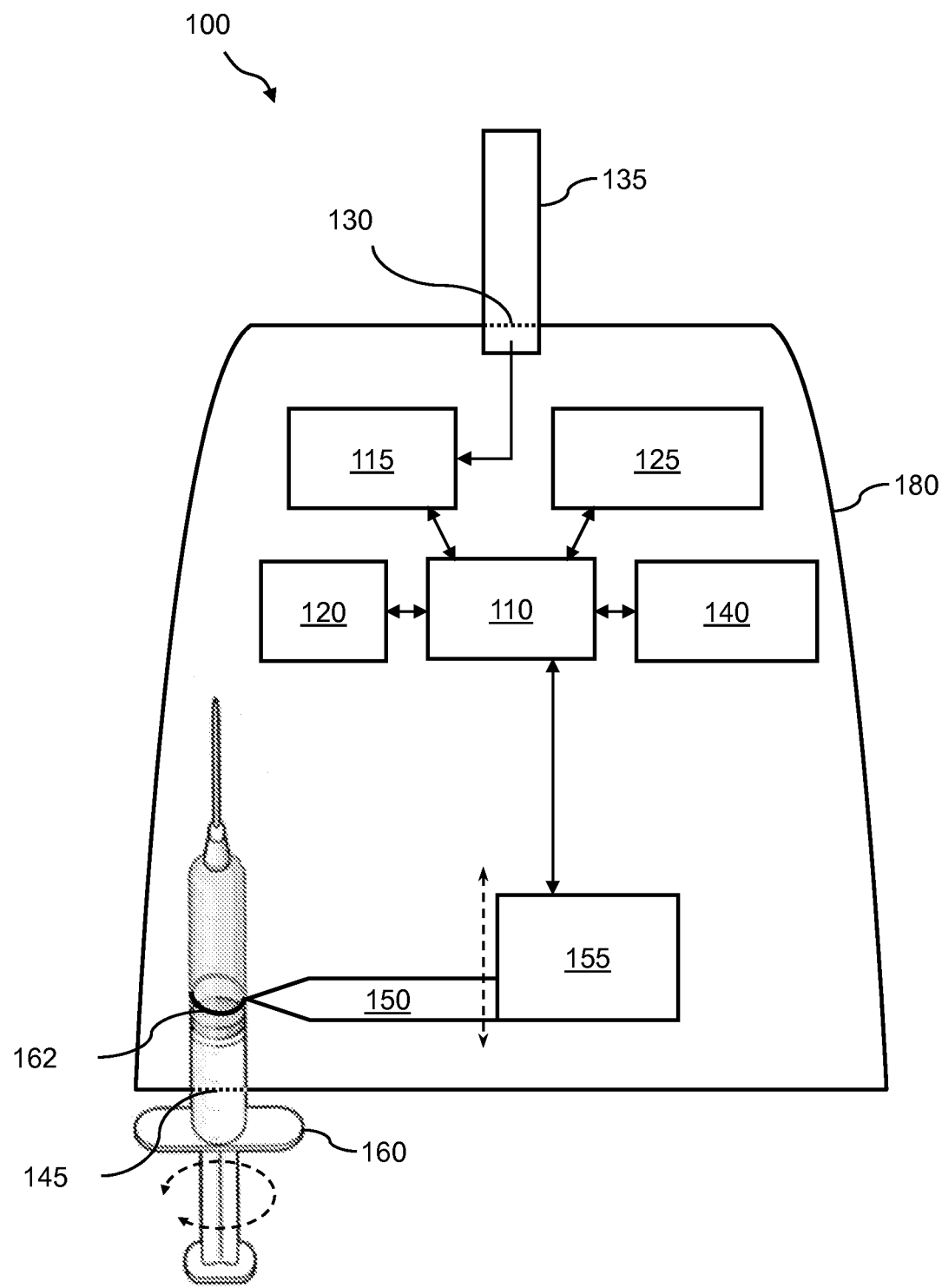
FIG. 1 illustrates a block diagram of an example of a multifunctional glucose monitoring system for measuring glucose level, determining insulin dosage, and indicating insulin dosage on a syringe.

FIG. 1 illustrates a block diagram of an example of a multifunctional glucose monitoring system 100 for measuring glucose level, determining insulin dosage, and indicating insulin dosage on a syringe. In this example, multifunctional glucose monitoring system 100 includes a controller 110, a transducer 115, a display 120, and a communication interface 125. Transducer 115, display 120, and communication interface 125 are operatively connected to controller 110. Controller 110, transducer 115, display 120, and communication interface 125 are arranged in a housing or body 180. Body 180 may, for example, be a molded plastic body. Additionally, body 180 includes a test port 130 into which, for example, one end of a disposable test strip 135 can be inserted and interfaced with transducer 115.

The controller 110, transducer 115, display 120, communication interface 125, and test strip 135 are the components of multifunctional glucose monitoring system 100 that are provided for measuring blood glucose levels in a manner that is well known. Controller 110 is, for example, any controller, microcontroller, processor, microprocessor, or digital signal processor (DSP) that is capable of executing program instructions with respect to managing the overall operations of multifunctional glucose monitoring system 100.

Transducer 115 detects the level of glucose in the blood sample on test strip 135 and converts the glucose level to an electrical signal that can be correlated to a glucose level. Transducer 115 is interfaced with controller 110. Controller 110 processes the electrical signal from transducer 115 by correlating the electrical signal to a glucose value, which is displayed to the user via display 120. Display 120 is, for example, a digital display (e.g., liquid crystal, LED, or the like) for displaying, among other things, the glucose value (i.e., the test results) as measured using transducer 115 and test strip 135. The test results may be displayed in milligrams per deciliter (mg/dL), millimoles per liter (mmol/L), or other suitable format/unit of measure. In addition to display 120, other standard user interface controls (not shown), such as push buttons, or indicators (not shown), such as LED indicators, may be integrated into body 180 of multifunctional glucose monitoring system 100.

Communication interface 125 is, for example, any wired or wireless communication link configured for long or short distance communication of, among other things, the test results to another computing device or system. For example, communication interface 125 can include wireless technology, such as Bluetooth® technology, Wi-Fi technology, IEEE 802.11 technology, infrared (IR) technology, and radio frequency (RF) technology; wired technology, such as a universal serial bus (USB) and/or an Ethernet port; and any combinations thereof.

Test strip 135 is a consumable element containing chemicals that react with glucose in the drop of blood used for each measurement, as is well known. In one example, test strip 135 is a plastic test strip with a small spot impregnated with glucose oxidase and other components. A test strip 135 is used once and then discarded. Alternatively, instead of test strips 135, multifunctional glucose monitoring system 100 can use discs that may be used for several readings, or other known technologies well known in the art.

In addition to the controller 110, transducer 115, display 120, communication interface 125, and test strip 135, which are the components of multifunctional glucose monitoring system 100 that are used for measuring blood glucose levels in a manner that is well known, multifunctional glucose monitoring system 100 includes mechanisms for determining the insulin dosage as well as mechanisms for indicating the insulin dosage on a syringe.

With respect to determining the insulin dosage, multifunctional glucose monitoring system 100 further includes a dosage algorithm 140 that is interfaced with or otherwise integrated into controller 110. Dosage algorithm 140 may be implemented in software or hardware. Dosage algorithm 140 is used to calculate the insulin dosage in "insulin units." Dosage algorithm 140 is used to calculate the insulin dose based, for example, on one or more of the following:

(1) type of insulin dose to be calculated, such as, but not limited to, the total daily insulin dose, the carbohydrate coverage insulin dose, the high blood sugar correction insulin dose, and the total mealtime insulin dose;
(2) patient information, such as, but not limited to, the patient's weight, height, gender, and age;
(3) glucose value (i.e., the test results) as measured using transducer 115 and test strip 135 and provided to dosage algorithm 140 by controller 110; and
(4) time of day.

In one example, dosage algorithm 140 calculates the "total daily insulin dose" in units of insulin using the following formula:

Patient's weight in pounds×0.25 or Patient's weight in kilograms×0.55.

In one example, dosage algorithm 140 calculates the "carbohydrate coverage insulin dose" in units of insulin using the following formula:

Total grams of carbohydrate in the meal÷Grams of carbohydrate disposed by 1 unit of insulin;

wherein the grams of carbohydrate disposed of by 1 unit of insulin is the denominator of the Insulin-to-carbohydrate (I:C) ratio.

In one example, dosage algorithm 140 calculates the "high blood sugar correction insulin dose" in units of insulin using the following formula:

(Actual blood sugar−Target blood sugar)÷Correction factor.

In one example, dosage algorithm 140 calculates the "total mealtime insulin dose" in units of insulin using the following formula:

Carbohydrate coverage insulin dose+High blood sugar correction insulin dose.

With respect to indicating the insulin dosage on a syringe (as calculated using dosage algorithm 140), multifunctional glucose monitoring system 100 further includes a syringe port 145, a built-in marker 150, and a marker drive mechanism 155. Syringe port 145 is an opening in body 180 through which the barrel of a syringe, such as a syringe 160, can be inserted, needle-end first, as shown in FIG. 1. Marker 150 can be any type of marking device capable of rendering a visually discernable mark 162 on the surface of the barrel of syringe 160, wherein the barrel is typically formed of plastic or glass. In one example, the mark 162 that is rendered via marker 150 is removable or erasable from the barrel of syringe 160. In this example, marker 150 may be a standard dry-erase marker. In another example, the mark 162 that is rendered via marker 150 is not removable or erasable from the barrel of syringe 160. In this example, marker 150 may be a standard permanent marker. Additionally, marker 150 may be a disposable marker that is discarded and replaced when the marking ink is depleted. Alternatively, marker 150 may be a refillable marker that can be refilled when the marking ink is depleted. Marker 150 may include a colored ink, such as a high visibility/contrast colored ink, or alternatively may include an additive to make the ink glow in the dark.

In yet a further alternative embodiment, marker 150 may be capable of etching a mark 162 directly onto the surface of the barrel of syringe 160, for example by using a sharpened point.

In still yet a further alternative embodiment, the marking device of marker 150 may include a strip of material capable of adhering to the barrel of syringe 160 to form the mark 162. In this alternative embodiment, the strip may be applied to the barrel of syringe 160, and may be colored, such as a high visibility/contrast color and/or have glow in the dark properties, so as to be readily visible to a user or caregiver. Additionally, the strip may include a transparent window in the marking strip to permit the user or caregiver to see a plunger tip positioned within the barrel of syringe 160. In this embodiment the plunger tip may also be colored in a high visibility/contrast color to permit the user or caregiver to easily discern the plunger tip positioned in the window of the marking strip.

Marker drive mechanism 155 is the mechanism for holding marker 150 and for positioning a tip of marker 150 against the surface of and moving along the length of the barrel of syringe 160. Marker drive mechanism 155 can be any mechanism for (1) securely holding marker 150 substantially orthogonal to the barrel of syringe 160, (2) holding the tip of marker 150 against the surface of the barrel of syringe 160, and (3) moving marker 150 along the length of the barrel of syringe 160. Additionally, marker 150 and marker drive mechanism 155 are sized and configured to fit within body 180. Marker drive mechanism 155 may be any suitable mechanism capable of performing the functions described above. In two examples, marker drive mechanism 155 may be a servo and worm gear arrangement or a stepper drive mechanism.

Marker drive mechanism 155 is interfaced with controller 110. Once, a glucose level test result is received by controller 110 and once dosage algorithm 140 has calculated the insulin dosage in insulin units, controller 110 provides instructions to marker drive mechanism 155 to move marker 150 to a position along the length of the barrel of syringe 160 that corresponds to the insulin units of the insulin dosage. Once the tip of marker 150 is moved into position against the barrel of syringe 160, a user (not shown) may rotate syringe 160 a certain amount up to 360 degrees. In so doing, the ink (or etch or strip as discussed above) from marker 150 is transferred to the barrel of syringe 160; namely, a dosage mark 162 is rendered on the barrel of syringe 160 as shown in FIG. 1. Once syringe 160 is removed from syringe port 145 of multifunctional glucose monitoring system 100, dosage mark 162 is clearly visible to the user at a certain insulin unit marking.

Controller 110, dosage algorithm 140, and marker drive mechanism 155 operate with the assumption that syringe 160 is a standard syringe for insulin users that has known fluid capacity, known dimensions, and standard markings in insulin units. Mechanisms are built into syringe port 145 to ensure the any syringe 160 that is inserted or docked therein is in a known position with respect to body 180 and/or marker drive mechanism 155. At the same time, syringe 160 is allowed to rotate within syringe port 145. More details of an example of syringe 160 that has been marked using marker 150 of multifunctional glucose monitoring system 100 are described with reference to FIG. 2.

Figure 2:
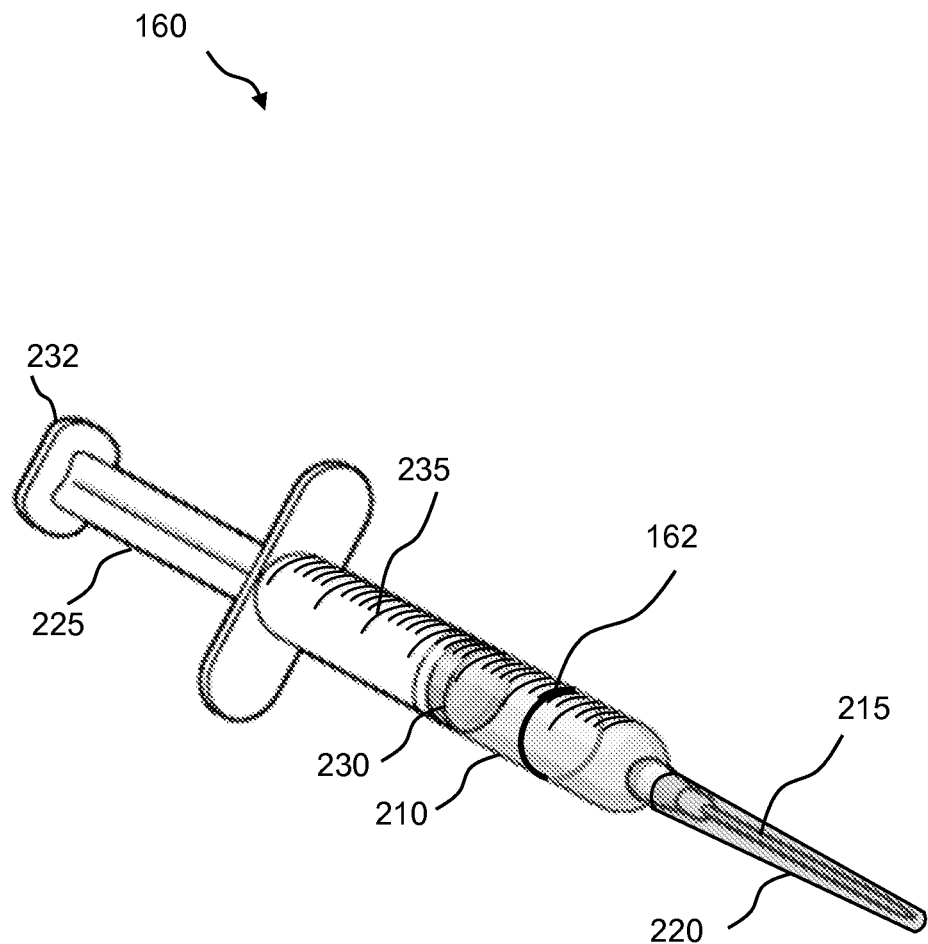
FIG. 2 illustrates an isometric view of an example of a syringe that has a dosage mark as provided using the multifunctional glucose monitoring system.

FIG. 2 illustrates an isometric view of an example of syringe 160 that has dosage mark 162, as provided using multifunctional glucose monitoring system 100 of FIG. 1. Syringe 160 is a standard syringe used for insulin injections. In one example, syringe 160 is a 50-insulin unit syringe. Syringe 160 includes a barrel 210 for holding a volume of liquid insulin and a needle 215 that is fluidly connected to one end of barrel 210. Optionally, a needle shield 220 is provided to protect needle 215. A plunger 225 is fitted into an open end of barrel 210. In particular, a plunger tip 230 (which may be visually enhanced, such as by coloring), at one end of plunger 225 is slideably fitted into barrel 210. A plunger cap 232 is provided at the opposite end of plunger 225, which provides a grip for the user of syringe 160. Barrel units 235, which indicate insulin units, are marked on or etched into the outer surface of barrel 210. In FIG. 2, barrel 210 of syringe 160 has a dosage mark 162 that has been applied using marker 150 of multifunctional glucose monitoring system 100. In this example, dosage mark 162 is a 360-degree marking around the perimeter of barrel 210.

Figure 3:
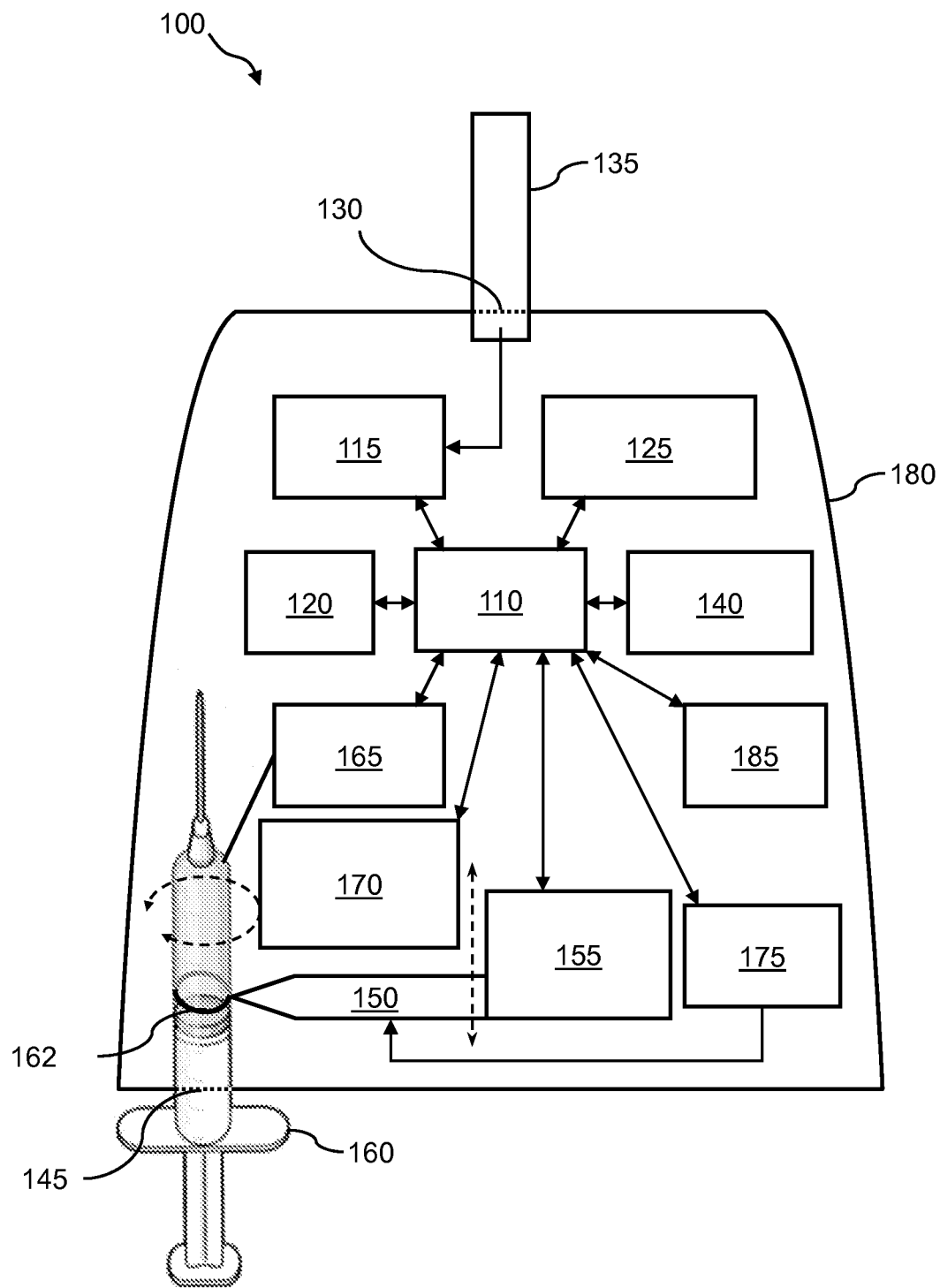
FIG. 3 illustrates a block diagram of another example of the multifunctional glucose monitoring system that includes additional features for enhancing the automation thereof.

FIG. 3 illustrates a block diagram of another example of multifunctional glucose monitoring system 100. Namely, FIG. 3 shows a configuration of multifunctional glucose monitoring system 100 that includes additional automation features. In this example, multifunctional glucose monitoring system 100 includes controller 110, transducer 115, display 120, communication interface 125, test port 130 in body 180 for accepting, for example, test strip 135, dosage algorithm 140, syringe port 145 in body 180 for accepting syringe 160, marker 150, and marker drive mechanism 155 as described with reference to FIG. 1. However, in this example, multifunctional glucose monitoring system 100 further includes a syringe sensor 165, a syringe drive mechanism 170, an ink level/strip sensor 175, and various indicators 185.

Syringe sensor 165 is used to sense whether a syringe 160 is successfully docked within syringe port 145. In one example, syringe sensor 165 may be a microswitch that toggles when syringe 160 is present vs. when not present. In another example, syringe sensor 165 may be an IR sensor that toggles when syringe 160 is present vs. when not present. In one example, the output of syringe sensor 165 may be used to enable marker drive mechanism 155 and/or syringe drive mechanism 170 only when syringe 160 is successfully docked. In another example, the output of syringe sensor 165 may be used to drive an indicator to the user that syringe 160 is successfully docked within syringe port 145. For example, the output of syringe sensor 165 may be used to control one of indicators 185. Namely, the output of syringe sensor 165 may control a "Syringe Ready" LED. Indicators 185 may be any visual indicators (e.g., LEDs), audible indicators (e.g., beep or buzz), tactile indicators (e.g., vibration), and any combinations thereof.

Instead of the user having to manually rotate syringe 160 in the process of rendering dosage mark 162 on the barrel of syringe 160, syringe drive mechanism 170 is a mechanism for automatically rotating syringe 160 without user interaction. Syringe drive mechanism 170 may be any suitable mechanism capable of performing the functions described above. In one example, syringe drive mechanism 170 drives a soft rubber wheel that is pressed against the surface of the barrel of syringe 160. When the wheel is rotated, syringe 160 is rotated. Syringe drive mechanism 170 may be activated by controller 110 once all operations of dosage algorithm 140 are complete and once marker 150 is queued up using marker drive mechanism 155.

Instead of the user having to visually observe that the dosage mark 162 is fading and, thus, conclude that the ink level of marker 150 is low, ink level/strip sensor 175 can be provided to automatically sense the ink level, or remaining strip quantity, in marker 150. Examples of ink level/strip sensor 175 may include sensing a plunger position on the ink dispenser, using light transmission through the ink dispenser reservoir, or approximating ink level based on a calculation of the number of turns of the syringe. The output of ink level/strip sensor 175 may be used to control one of indicators 185. For example, the output of ink level/strip sensor 175 may control a "Low Ink" LED.

Figure 4:
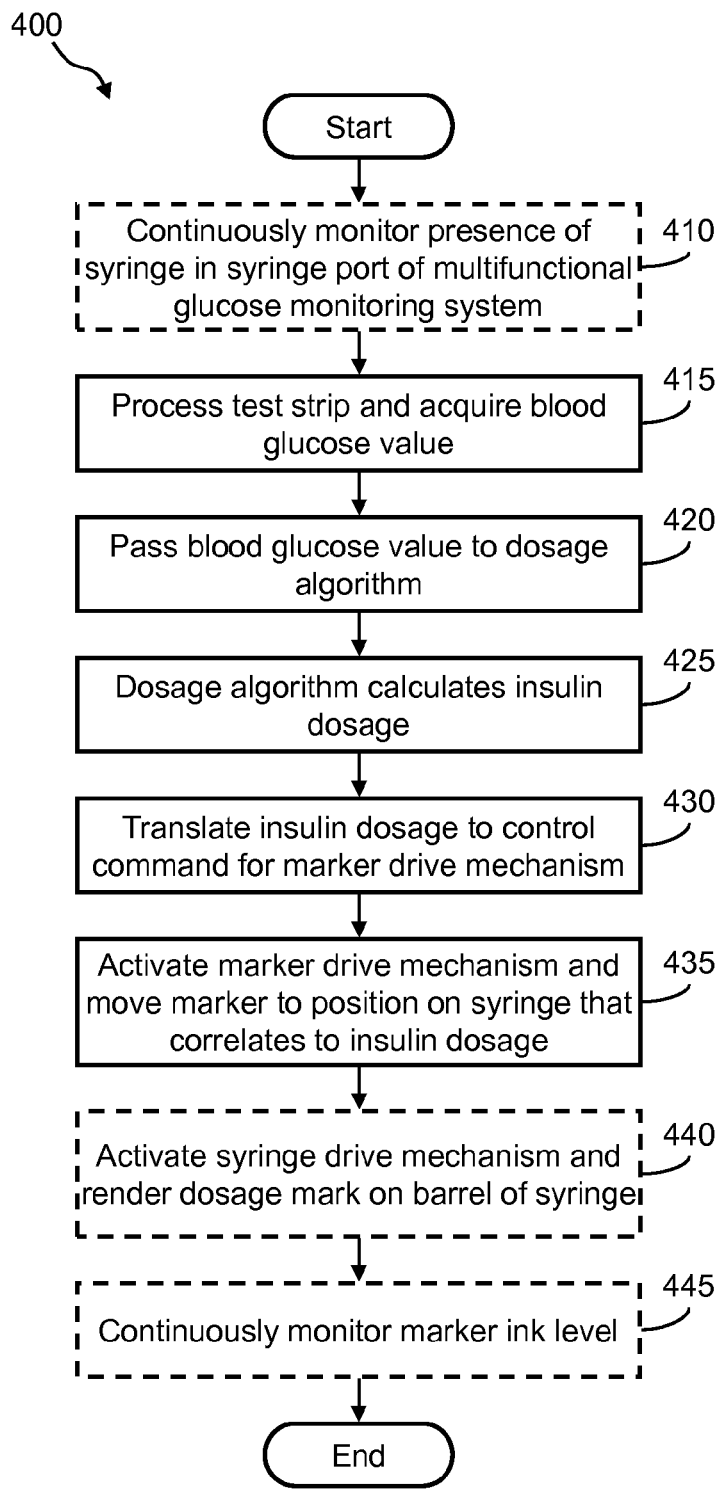
FIG. 4 illustrates a flow diagram of an example of a method of operation of the multifunctional glucose monitoring system.

FIG. 4 illustrates a flow diagram of an example of a method 400 of operation of multifunctional glucose monitoring system 100. When using the configuration of multifunctional glucose monitoring system 100 shown in FIG. 3, optional steps 410, 440, and 445 (shown with dashed lines) are included in method 400. However, when using the configuration of multifunctional glucose monitoring system 100 shown in FIG. 1, optional steps 410, 440, and 445 are omitted from method 400. Method 400 may include, but is not limited to, the following steps.

At an optional step 410, the presence of syringe 160 in syringe port 145 of multifunctional glucose monitoring system 100 is continuously monitored using syringe sensor 165. The state of syringe sensor 165 is monitored by controller 110 and used, for example, to enable or disable marker drive mechanism 155, to enable or disable syringe drive mechanism 170, to control a "Syringe Ready" LED or display a "Syringe Ready" message on display 120, or any combinations thereof.

At a step 415, test strip 135 that has the patient's blood sample is processed and a blood glucose reading is acquired. For example, transducer 115 detects the level of glucose in the blood sample on test strip 135 and converts the glucose level to an electrical signal that can be correlated to the glucose level. Controller 110 processes the electrical signal from transducer 115 and displays the test result (e.g., glucose value) on display 120. A normal blood glucose level is typically between about 70 and 120 mg/dL, a value below this range is typically considered a low blood glucose level, while a value above this range is typically considered a high blood glucose level.

At a step 420, controller 110 passes the test result (e.g., glucose value) to dosage algorithm 140.

At a step 425, dosage algorithm 140 calculates the insulin dosage based on the test result and any other useful input parameters. Namely, dosage algorithm 140 performs one or more insulin dosage calculations. For example, dosage algorithm 140 may calculate the total daily insulin dose, the carbohydrate coverage insulin dose, the high blood sugar correction insulin dose, and/or the total mealtime insulin dose. The calculation to perform can be user-defined, or may be based on some other input parameter such as time of day. In one example, dosage algorithm 140 calculates the insulin dosage to be 30 insulin units.

At a step 430, controller 110 receives the insulin dosage from dosage algorithm 140 and translates the insulin dosage to a control command for marker drive mechanism 155. For example, for an insulin dosage of 30 insulin units, a control command is generated to marker drive mechanism 155 that correlates to positioning the tip of marker 150 at the 30 insulin units mark on the barrel of syringe 160.

At a step 435, marker drive mechanism 155 is activated and moves marker 150 to a position along the barrel of syringe 160 that correlates to the insulin dosage calculated in step 425. For example, marker drive mechanism 155 is activated and processes the command from controller 110 to mark 30 insulin units. As a result, marker drive mechanism 155 moves the tip of marker 150 to the 30 insulin units position on the barrel of syringe 160.

At an optional step 440, syringe drive mechanism 170 is activated. In so doing, syringe 160 is rotated, for example, a full 360 degrees. Thereby rendering a 360 degree-dosage mark 162 on the barrel of syringe 160.

At an optional step 445, the ink level of marker 150 is continuously monitored using ink level sensor 175. In one example, controller 110 monitors the state of ink level sensor 175 to control, for example, a "Low Ink" LED or display a "Low Ink" message on display 120.

Figure 5:
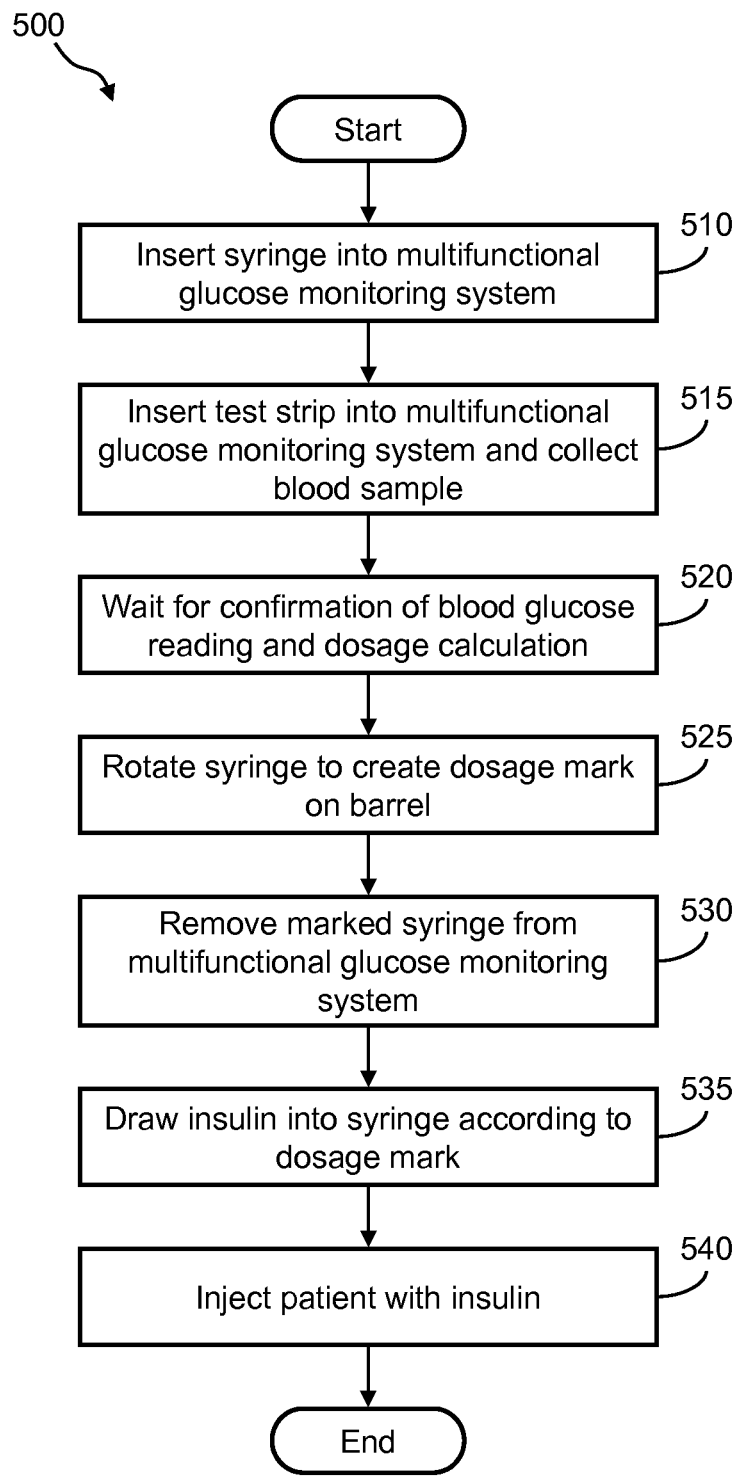
FIG. 5 illustrates a flow diagram of an example of a method of using the multifunctional glucose monitoring system.

FIG. 5 illustrates a flow diagram of an example of a method 500 of using multifunctional glucose monitoring system 100. Method 500 may include, but is not limited to, the following steps.

At a step 510, a user inserts a needle-end of syringe 160 into syringe port 145 of multifunctional glucose monitoring system 100.

At a step 515, the user inserts test strip 135 into test strip port 130 of multifunctional glucose monitoring system. Then, the user collects a blood sample on test strip 135.

At a step 520, the user monitors the display 120 or any other indicators and waits for confirmation of the blood glucose reading and dosage calculation. Without user interaction, marker 150 is automatically queued up for marking the barrel of syringe 160.

At a step 525, syringe 160 is rotated to create dosage mark 162 on the barrel of syringe 160. In one example, the user manually rotates syringe 160 to create dosage mark 162. In another example, syringe drive mechanism 170 is used to rotate syringe 160 and create dosage mark 162.

At a step 530, the user removes the marked syringe 160 from syringe port 145 of multifunctional glucose monitoring system 100.

At a step 535, the user draws an amount of insulin into the barrel of syringe 160 up to the dosage mark 162.

At a step 540, the patient is injected with the insulin using the marked syringe 160.

Figure 6:
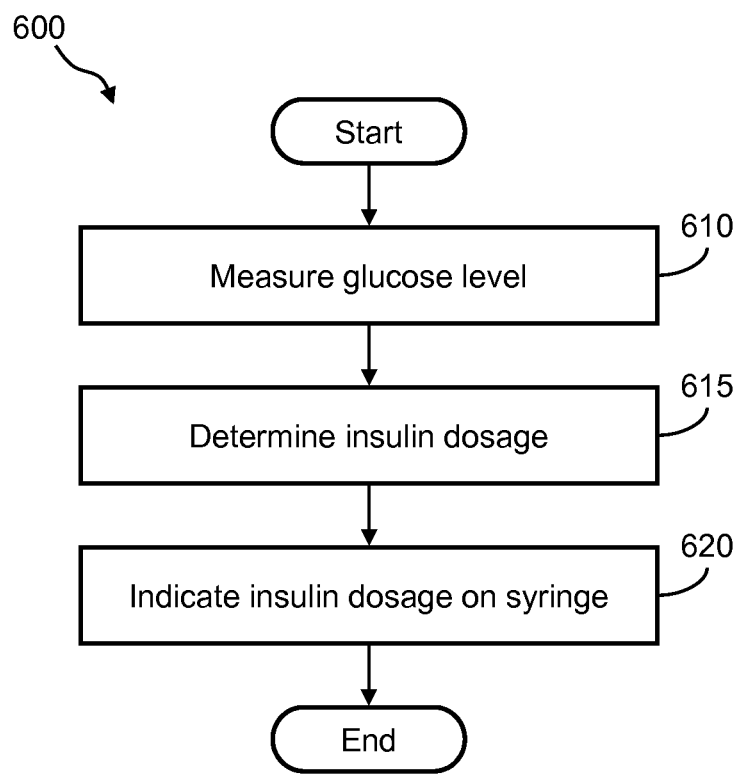
FIG. 6 illustrates a flow diagram of an example of a method of operation of the multifunctional glucose monitoring system according to a minimum configuration.

FIG. 6 illustrates a flow diagram of an example of a method 600 of operation of multifunctional glucose monitoring system 100 according to a minimum configuration. Method 600 may include, but is not limited to, the following steps.

At a step 610, a blood glucose reading is acquired using test strip 135, transducer 115 and controller 110.

At a step 615, an insulin dosage is calculated via dosage algorithm 140 based on the reading acquired in step 610 and any other useful input parameters.

At a step 620, using marker 150 and marker drive mechanism 155, syringe 160 is marked according to the insulin dosage calculated in step 615.

Other features that can be incorporated into multifunctional glucose monitoring system 100 may include, but are not limited to, the following.

Figure 7:
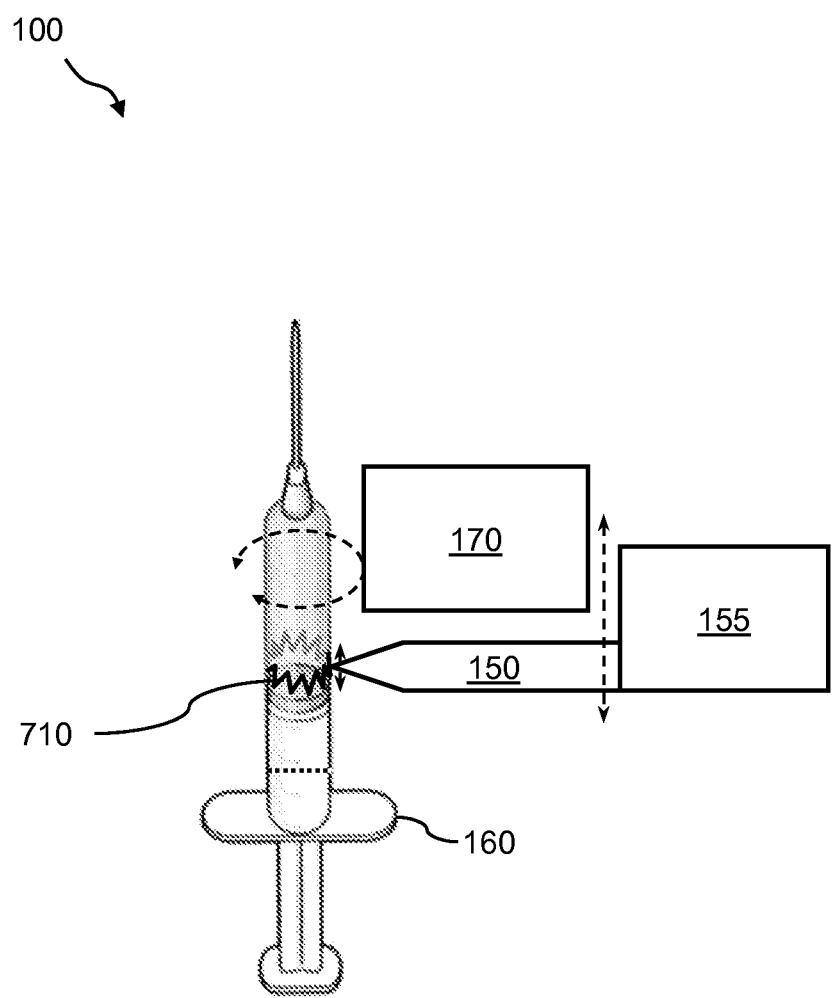
FIG. 7 illustrates a block diagram of a portion of the multifunctional glucose monitoring system, showing a technique of marking an insulin range or window on the syringe.

(1) the dosage mark that is marked on the barrel of syringe 160 may indicate a dosage range or window instead of a finite dosage. For example and referring now to FIG. 7, using controller 110, the operations of marker drive mechanism 155 and syringe drive mechanism 170 may be coordinated to form a zigzag marking pattern (e.g., a dosage range mark 710) on the barrel of syringe 160, wherein the points of the zigzag marking pattern indicate the upper and lower boundaries of the dosage range or window, alternatively the operations of marker drive mechanism 155 and syringe drive mechanism 170 may be coordinated to form lines (e.g., 2) spaced apart, wherein the lines indicate an upper and lower boundaries of the dosage range or window;

(2) the ink in marker 150 may glow in the dark or in dim lighting conditions;

(3) using syringe sensor 165, upon sensing that the marked syringe 160 is removed from multifunctional glucose monitoring system 100, controller 110 can automatically store any useful information in memory (not shown). Useful information may include, but is not limited to, the glucose reading, the insulin dosage, a timestamp, a caregiver ID, and/or a patient ID; and (4) using syringe sensor 165, upon sensing that the marked syringe 160 is removed from multifunctional glucose monitoring system 100, controller 110 can automatically transmit (via communication interface 125) any useful information to an external computing device, system, or network. Again, useful information may include, but is not limited to, the glucose reading, the insulin dosage, a timestamp, a caregiver ID, and/or a patient ID.

CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicant's invention set forth in this specification, and neither its use nor its absence is intended to limit the scope of the applicants' invention or the scope of the claims. This specification is divided into sections for the convenience of the reader only. Headings should not be construed as limiting of the scope of the invention. It will be understood that various details of the present invention may be changed without departing from the scope of the present invention. Furthermore, the foregoing description is for the purpose of illustration only, and not for the purpose of limitation.

We claim:

1. A multifunction glucose meter, comprising:
a syringe port formed in a body of the multifunction glucose meter, wherein the syringe port is configured to accept a syringe;
a marking device, wherein the marking device is configured to place a mark on an exterior surface of a barrel of the syringe inserted into the syringe port;
a drive mechanism operatively connected to the marking device and configured to move the marking device along the length of the barrel of the syringe and into contact with the exterior surface of the barrel of the syringe inserted into the syringe port;
a test port; transducer; display and controller, wherein the test port is in operative communication with the transducer, and wherein the transducer and display are operatively connected to the controller;

a dosage algorithm that is interfaced with or integrated into the controller, wherein the dosage algorithm calculates an insulin dosage;

and wherein the controller linearly positions the marking device in accordance with the insulin dosage, and the marking device is positioned so as to place the marking device in contact with the exterior surface of the barrel of the syringe.

2. The meter of claim 1, wherein the dosage algorithm is implemented in at least on of software and hardware.

3. The meter of claim 1, wherein the mark is calibrated to indicate a particular dosage of insulin.

4. The meter of claim 3, wherein the calibration of the insulin dosage is based on a glucose reading performed by the glucose meter.

5. The meter of claim 4, wherein the mark on the barrel of the syringe indicates a point at which the barrel of the syringe is to be filled to provide the insulin dosage in accordance with the glucose reading from the glucose meter.

6. The meter of claim 1, further comprising a communication interface connected to the controller.

7. The meter of claim 1, further comprising at least one of a syringe sensor, ink level sensor, and marking strip level sensor.

8. The meter of claim 7, further comprising one or more indicators corresponding to the at least one of the syringe sensor, ink level sensor, and marking strip level sensor, wherein the one or more indicators are one of visual, audible, tactile, or combination thereof.

9. The meter of claim 1, wherein the marking device is disposed internally to the glucose meter and is proximate to the syringe port.

10. The meter of claim 9, wherein the syringe accepted into the syringe port is rotatable.

11. The meter of claim 10, further comprising a syringe drive mechanism proximate the syringe port and configured for rotating the syringe.

12. The meter of claim 1, wherein the marking device is rotatable about the exterior surface of the barrel of the syringe.

13. The meter of claim 1, where the marking device causes a mark on at least a portion of the barrel of the syringe.

14. The meter of claim 1, wherein the mark comprises an ink marking.

15. The meter of claim 14, wherein the ink marking comprises a high visibility/contrast color.

16. The meter of claim 1, wherein the mark comprises a strip adhered to the exterior surface of the barrel of the syringe.

17. The meter of claim 16, wherein the strip comprises a substantially transparent window formed therein.

* * * * *